(12) United States Patent
Pickett et al.

(10) Patent No.: US 11,903,225 B2
(45) Date of Patent: Feb. 13, 2024

(54) PHOTODETECTORS BASED ON TWO-DIMENSIONAL QUANTUM DOTS

(71) Applicant: Nanoco 2D Materials Limited, Manchester (GB)

(72) Inventors: Nigel Pickett, East Croydon (GB); Stuart Stubbs, Manchester (GB); Nathalie Gresty, Chester (GB)

(73) Assignee: NANOCO 2D MATERIALS LIMITED

( * ) Notice: Subject to any disclaimer, the term of this patent is extended or adjusted under 35 U.S.C. 154(b) by 0 days.

(21) Appl. No.: 17/703,679

(22) Filed: Mar. 24, 2022

(65) Prior Publication Data
US 2022/0216438 A1  Jul. 7, 2022

Related U.S. Application Data

(62) Division of application No. 16/544,181, filed on Aug. 19, 2019, now abandoned.
(Continued)

(51) Int. Cl.
*H10K 30/35* (2023.01)
*G01N 33/58* (2006.01)
(Continued)

(52) U.S. Cl.
CPC ............ *H10K 30/35* (2023.02); *C09K 11/681* (2013.01); *G01N 33/588* (2013.01);
(Continued)

(58) Field of Classification Search
CPC .. C09K 11/681; G01N 33/588; G02B 6/0229; H01L 31/035209; H01L 31/035218;
(Continued)

(56) References Cited

U.S. PATENT DOCUMENTS 6,559,375 B1   5/2003  Meissner et al.
2013/0263918 A1*  10/2013  Konstantatos .... H01L 31/03925
                                                257/14
(Continued)

FOREIGN PATENT DOCUMENTS

WO   2015031835 A1   3/2015

OTHER PUBLICATIONS

Mu et al. Photodetectors based on sensitized two-dimensional transition metal dichalcogenides—a review. J. Mater. Res. vol. 32, No. 22, Nov. 28, 2017, pp. 4115-4131 (Year: 2017).*
(Continued)

*Primary Examiner* — Galina G Yushina
(74) *Attorney, Agent, or Firm* — Blank Rome LLP

(57) ABSTRACT

A photodetector includes a first electrode; an interlayer disposed on the first electrode; a photoabsorbing layer disposed on the interlayer, the photoabsorbing layer having one or more charge transport materials, and a plurality of two-dimensional quantum dots (2D QDs) dispersed in the one or more charge transport material; and a second electrode disposed on the photoabsorbing layer. A heterostructure photodetector includes a first electrode; a first photoabsorbing layer disposed on the first electrode, the first photoabsorbing layer having a first photoabsorbing material; a second photoabsorbing layer disposed on the first photoabsorbing layer, the second photoabsorbing layer having a second photoabsorbing material; and a second electrode disposed on the second photoabsorbing layer.

11 Claims, 4 Drawing Sheets

Related U.S. Application Data

(60) Provisional application No. 62/722,006, filed on Aug. 23, 2018.

(51) Int. Cl.
  *C09K 11/68* (2006.01)
  *G02B 6/02* (2006.01)
  *H10K 85/10* (2023.01)

(52) U.S. Cl.
  CPC .......... *G02B 6/0229* (2013.01); *H10K 85/113* (2023.02); *H10K 85/151* (2023.02)

(58) Field of Classification Search
  CPC .... H01L 31/109; H10K 30/35; H10K 85/113; H10K 85/1135; H10K 85/115; H01K 85/151; Y02E 10/549
  See application file for complete search history.

(56) References Cited

U.S. PATENT DOCUMENTS

| | | | | |
|---|---|---|---|---|
| 2015/0075606 | A1* | 3/2015 | Lee | H10K 77/111 136/256 |
| 2016/0233447 | A1* | 8/2016 | Kim | H10K 50/80 |
| 2017/0117496 | A1* | 4/2017 | Koh | H10K 50/16 |
| 2018/0130843 | A1 | 5/2018 | Jo et al. | |
| 2018/0216000 | A1* | 8/2018 | Daniels | C09K 11/572 |

OTHER PUBLICATIONS

Tian et al. Hybrid Nanostructures for Photodetectors, Advanced Optical Materials, 2017, 6, 1600468 (Year: 2017).*

Li et al. Single-Layer Single-Crystalline SnSe Nanosheets, Journal of the American Chemical Society, 135, pp. 1213-1216 (Year: 2013).*

Trend on band alignments: Validity of Anderson's rule in SnS2 and SnSe2-based van der Waals heterostructures, Physical Review B 97, 165402 (2018). The referenced figure by the Office Action refers to Koda et al. J. Phys. Chem. C120, 10895, 2016 (Year: 2018).*

Huang et al. Highly sensitive photodetectors based on hybrid 2D-0D SnS2-copper indium sulfide quantum dots, Appl. Phys. Lett. 108, 013101 (2016) (Year: 2016).*

Tian et al. Hybrid Nanostructures for Photodetectors. Adv. Optical Matter 2017, 5, 160048 (Year: 2017).*

Jingzhi Shang, et al., "Light Sources and Photodetectors Enabled by 2D Semiconductors", Small Methods 2, 1800019, 2018, DOI: 10.1002/smtd.201800019, 15 pgs.

R R LaPierre et al., "A review of III-V nanowire infrared photodetectors and sensors" J. Phys. D: Appl. Phys., 50 123001, 2017, 11 pgs.

Monica Esopi et al., "Tuning the spectral response of ultraviolet organic-inorganic hybrid photodetectors via charge trapping and charge collection narrowing" Phys. Chem. Chem. Phys., 20, 11273-11284, 2018.

* cited by examiner

PHOTODETECTORS BASED ON TWO-DIMENSIONAL QUANTUM DOTS

CROSS-REFERENCE TO RELATED APPLICATIONS

This application is a divisional of U.S. Non-Provisional application Ser. No. 16/544,181 filed Aug. 19, 2019, which claims the benefit of U.S. Provisional Application No. 62/722,006 filed Aug. 23, 2018, the entire contents of each of which are incorporated by reference herein.

BACKGROUND OF THE INVENTION

1. Field of the Invention

The present invention generally relates to semiconductor nanoparticles commonly called "quantum dots" (QDs). More particularly, it relates to quantum dots comprised of two-dimensional material and their use in photodetectors.

2. Description of the Related Art Including Information Disclosed Under 37 CFR 1.97 and 1.98

A photodetector is a device that produces an electrical signal in response to incident photons. Photodetectors or photosensors are responsive to the intensity of light or other electromagnetic energy incident upon them. A solid-state photodetector has a p-n junction that converts photons of light into an electrical current. The absorbed photons make electron-hole pairs in the depletion region. Photodiodes, photoconductors and phototransistors are examples of photodetectors. In a sense, solar cells are photodetectors inasmuch as they convert some of the light energy they absorb into electrical energy, the quantity of which may be sensed by appropriate circuitry.

A photodiode is typically based on a p-n junction. In a photodiode, when a photon of sufficient energy strikes the device, an electron-hole pair is created. If the absorption occurs in the junction's depletion region, or one diffusion length away from it, the built-in electric field of the depletion region leads to the carriers being swept from the junction, with holes moving towards the anode and electrons towards the cathode, producing a photocurrent.

A photoconductor is a device that detects a temporary change in conductivity of a semiconductor that results from the illumination with light. Photons generate photoexcited carriers, which are extracted by an electric field generated through a voltage bias that is applied between the electrodes.

A phototransistor is similar to a photodiode, with the addition of a further n-type region. The phototransistor includes a photodiode with internal gain. It can be represented as a bipolar transistor enclosed in a transparent case such that photons can reach the base-collector junction. Electrons that are generated from photons in the base-collector junction are injected into the base, amplifying the current.

The three types of photodetector each have different properties, so are useful for different applications. Phototransistors and photodiodes detect at a similar rate, but phototransistors have a slower response time (microseconds vs. nanoseconds for a photodiode). Phototransistors have a higher gain, while photodiodes vary less with temperature.

Photodetectors may be used in different configurations. Single sensors may detect overall light levels. A 1-D array of photodetectors, as in a spectrophotometer or a line scanner, may be used to measure the distribution of light along a line. A 2-D array of photodetectors may be used as an image sensor to form images from the pattern of light incident upon it.

A photodetector or array is typically covered by an illumination window which may have an anti-reflective coating.

There are a number of performance metrics (so-called "figures of merit") by which photodetectors may be characterized and compared. One performance metric is spectral response (the response of a photodetector as a function of photon frequency). Another performance metric is quantum efficiency (QE; the number of carriers (electrons or holes) generated per photon). Yet another performance metric is responsivity (R; The output current divided by total light power falling upon the photodetector. $R=QE/E_{photon}$, where $E_{photon}$ is the photon energy in eV). Yet another performance metric is noise-equivalent power (NEP; the minimum detectable power, i.e., the optical signal at which the electrical signal-to-noise ratio in the detector is equal to unity (0 dB), when the bandwidth is limited to 1 Hz). Yet another performance metric is specific detectivity (D*; the square root of the detector area, A, multiplied by the frequency bandwidth, B, divided by the noise equivalent power; $D^*=[\sqrt{(AB)}]/NEP$). Yet another performance metric is gain (G; the output current of a photodetector divided by the current directly produced by the photons incident on the detectors, i.e., the built-in current gain). Yet another performance metric is dark current ($I_d$; the current flowing through a photodetector even in the absence of light). Yet another performance metric is response time (τ; the time needed for a photodetector to go from 10% to 90% of final output). Yet another performance metric is noise spectrum (the intrinsic noise voltage or current as a function of frequency; this can be represented in the form of a noise spectral density). Yet another performance metric is nonlinearity (the RF-output is limited by the nonlinearity of the photodetector). Yet another performance metric is spectral selectivity (the cut-off wavelength beyond which the response signal is comparable or smaller to the noise level.

To achieve photodetector high performance, a combination of a high responsivity, short response time, high specific density, and a broad spectral selectivity wavelength range is desirable.

There is increasing interest in solution-processable photodetectors with sensitivity spanning the ultraviolet (UV) to the near-infrared (NIR) range, for applications such as imaging sensors. Of particular interest is the 1-1.8 µm range, where water absorption is low.

The potential use of colloidal quantum dots (QDs) as photoabsorbers for photodetection applications has been recognized, with research largely focusing on PbS QDs containing toxic lead.

2D materials, including graphene and transition metal dichalcogenides (TMDCs), have been investigated as photoabsorbers for photodetection applications, due to a combination of their optical properties and mechanical flexibility. Photodetectors based on graphene have been extensively investigated and shown to exhibit high carrier mobility, excellent stability, high mechanical strength, and a spectral response spanning the visible to the far-IR. However, difficulties in opening up graphene's band gap have led to a high dark current, limiting its applicability to photodetection. Layered TMDCs offer many advantages, including a band gap that can be tuned by the number of layers. They are also compatible with complementary metal-oxide-semiconductor (CMOS) technology, which can be used to construct integrated circuits, enabling the development of multifunctional, high performance photodetectors with low power consumption.

Photodetectors with a high responsivity, broadband spectral and high detectivity are currently difficult to produce using a single TMDC due to their narrow thickness, which limits light absorption. Use of a highly absorbing sensitizer can help to improve the light absorption efficiency, yet the sensitizer needs to be sufficiently thin to retain the merits of a 2D material. High carrier mobility and a band structure aligning well with that of the TMDCs is also desirable for efficient charge separation and transfer.

Colloidal QDs have been used as sensitizers in combination with TMDC sheets to realize sensitive, fast and broadband photodetectors. For example, PbS QDs have been used in combination with $WSe_2$ nanosheets, [C. Hu et al., *Adv. Funct. Mater.* 2017, 27, 1603605] and CdS/ZnS QDs have been combined with $WS_2$ monolayers. [A. Baulesbaa, K. Wang, M. Mahjouri-Somani, M. Tian, A. A. Puretzky, I. Ivanov, C. M. Rouleau, K. Xiao, B. G. Sumpter and D. B. Grohegan, *J. Am. Chem. Soc.*, 2016, 138, 14713]

Compared with QDs, nanosheets have a larger contact area, so hybrid devices with 2D nanosheets of materials such as graphene and other layered materials in conjunction with TMDCs have been investigated. For devices with a 2D heterostructure as the sensitizer, formation of the Schottky barrier at the heterostructure interface can result in an inherent electronic field to provide efficient charge transfer at the interface.

Thus, both colloidal QDs and 2D nanosheets can provide advantages for photodetector applications.

Crystalline silicon has traditionally been used for photodetection applications. However, its absorption is limited to below 1.1 μm, which means that it fails to absorb the majority of the IR spectrum. In addition, its absorption is weak within its spectral range, only exceeding 104 cm⁻ at 500 nm. Within the UV region, at wavelengths relevant for the detection of skin cancer, the ultrashort absorption wavelengths in silicon lead to the generation of electron-hole pairs near to the highly recombinative surface states. This limits the UV sensitivity in standard silicon devices. There has therefore been great interest in materials that can absorb light beyond the range of silicon.

Epitaxially grown QDs have been used for photodetection applications but can be difficult to process. All-organic semiconductors may offer ease of handling for photodetection applications. However, until recently there have been few small organic molecules or polymers available with narrow bandgaps suitable for the manufacture of photodiodes in the near infrared range.

QD photodiode devices can be tuned into the near infrared range, beyond the spectral range of organic semiconductors, but a major concern has been the reliance on QDs based on toxic heavy metals such as lead or cadmium.

Photodetectors incorporating photoabsorbers based on 2D materials, such as graphene and TMDCs, have been explored. Advantages include their unique optical characteristics and mechanical flexibility. Other desirable properties include high carrier mobility, chemical stability, mechanical strength, and a spectral response that can be tuned from the visible to the far-IR regions. In particular, photodetectors based on TMDCs can be tuned by varying the number of layers. Heterostructures of two different layered materials have also been explored. The weak van der Waals interaction between two favorably disposed materials may create a high-quality heterojunction without introducing problems due to lattice mismatch between the two materials.

A heterostructure device comprising CdSe-based 2D nanoplatelets and graphene, has been described. [A. Robin, E. Lhuillier and B. Dubertret, *MRS Adv.*, 2016, 2187; A. Robin, E. Lhuillier, X. Z. Xu, S. Ithurria, H. Aubin, A. Ouerghi and B. Dubertret, *Sci. Rep.*, 2016, 6, 24909]. This device takes advantage of the strong absorbance of the nanoplatelets and the high carrier mobility of graphene. The 2D nanoplatelets have thicknesses between 1-5 nm and lateral dimensions up to 1 μm, such that the lateral dimensions are much larger than the Bohr radius. A disadvantage of these nanoplatelets is that they fail to offer bandgap tuneability.

For photodetectors incorporating layers of 2D materials, one issue which must be addressed is the elimination of deep-level trap states, which are detrimental to response speed.

Though a number of photodetector devices incorporating 2D materials have been reported, the prior art relies upon exfoliation or CVD-deposition processes that are difficult to scale.

BRIEF SUMMARY OF THE DISCLOSURE

Photodetectors according to various aspects of the disclosure may comprise a plurality of semiconductor nanoparticles with lateral dimensions in the quantum confinement regime and having a thickness between 1 and 5 atomic or molecular monolayers, inclusive ("2D quantum dots" or "2D QDs").

Some of the advantages of using QDs in photodetector applications include a strong, tunable absorption spectrum and solution processability. Some of the advantages of using 2D materials include a high contact area and surface flatness, tuneability of the absorption via the thickness of the material, high mobility and high transparency.

By using 2D QDs, rather than other conventional forms of QDs (i.e., 0D spherical QDs, 1D QDs, for example nanorods, or 3D QDs, for example nanocubes, nanotetrapods, nanopyramids, etc.) and/or 2D layered materials, the combined advantages of QDs and 2D materials can be realized. Additional absorption tuneability may be achieved by modifying the QD thickness and 2D QDs may be composed of non-toxic materials, alleviating the concerns over the toxicity of QDs based on heavy metals such as cadmium and lead.

Solution-processable photodetectors have particular benefits in sensor applications.

BRIEF DESCRIPTION OF THE DRAWING(S)

DETAILED DESCRIPTION OF THE INVENTION

Figure 1:
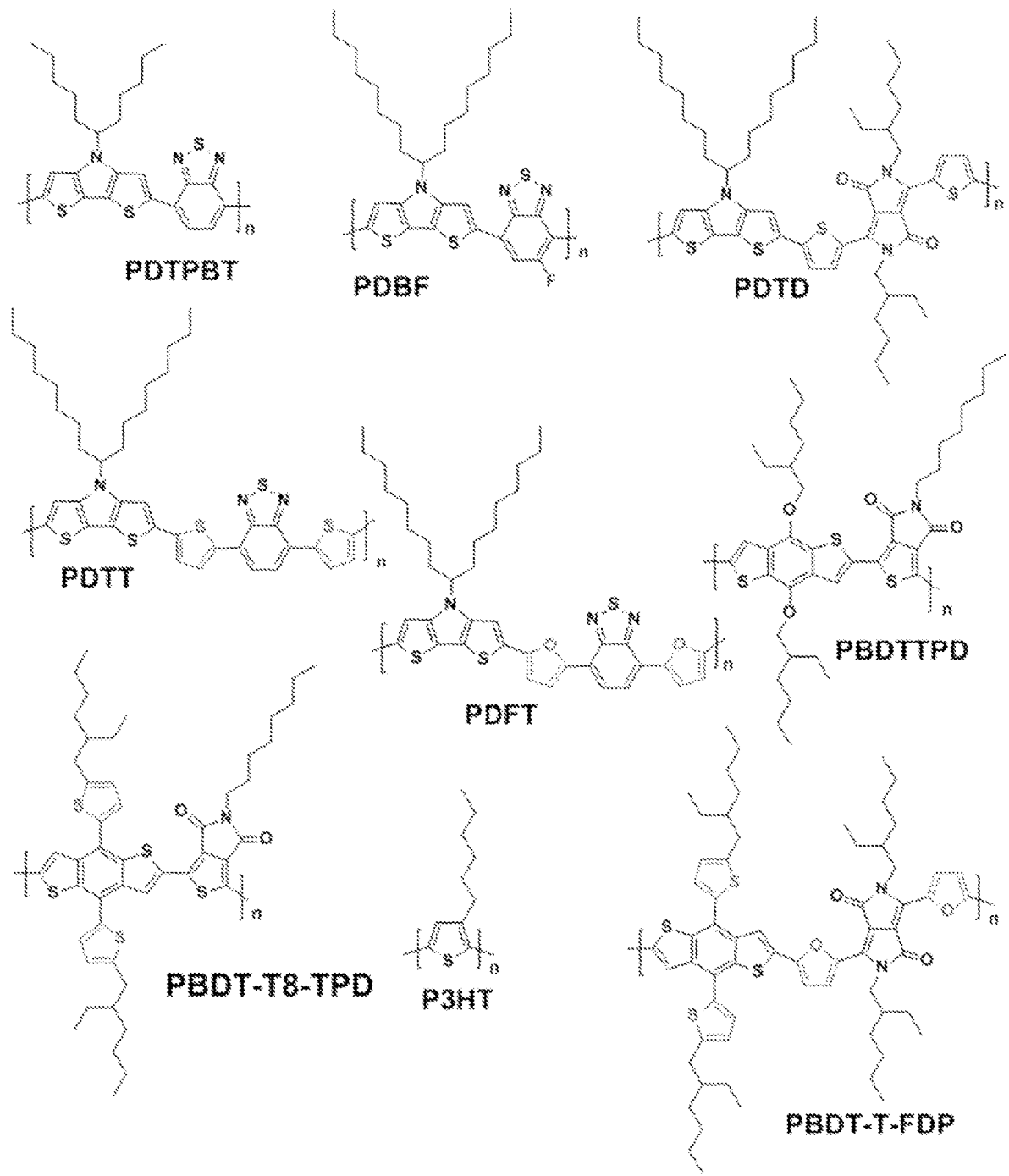
FIG. 1 illustrates chemical structures of various charge-transporting polymers which may be combined with 2D QDs to produce a 2D QD-sensitized organic photodiode in accordance with various aspects of the disclosure.

The following description of the embodiments is merely exemplary in nature and is in no way intended to limit the subject matter of the present disclosure, their application, or uses.

As used throughout, ranges are used as shorthand for describing each and every value that is within the range. Any value within the range can be selected as the terminus of the range. Unless otherwise specified, all percentages and amounts expressed herein and elsewhere in the specification should be understood to refer to percentages by weight.

For the purposes of this specification and appended claims, unless otherwise indicated, all numbers expressing quantities, percentages or proportions, and other numerical values used in the specification and claims, are to be understood as being modified in all instances by the term "about." The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±10 percent, alternatively±5 percent, and alternatively±1 percent of the given numeric value provided such a deviation does not alter the end function or result of the value. Accordingly, unless indicated to the contrary, the numerical parameters set forth in this specification and attached claims are approximations that can vary depending upon the desired properties sought to be obtained by the present invention.

It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. For example, as used in this specification and the following claims, the terms "comprise" (as well as forms, derivatives, or variations thereof, such as "comprising" and "comprises"), "include" (as well as forms, derivatives, or variations thereof, such as "including" and "includes") and "has" (as well as forms, derivatives, or variations thereof, such as "having" and "have") are inclusive (i.e., open-ended) and do not exclude additional elements or steps. Accordingly, these terms are intended to not only cover the recited element(s) or step(s), but may also include other elements or steps not expressly recited. Furthermore, as used herein, the use of the terms "a" or "an" when used in conjunction with an element may mean "one," but it is also consistent with the meaning of "one or more," "at least one," and "one or more than one." Therefore, an element preceded by "a" or "an" does not, without more constraints, preclude the existence of additional identical elements.

Research into the properties of colloidal QDs and the development of optoelectronic devices thereof have been of major interest for over 20 years. More recently, there has been increasing interest in the unusual properties of two-dimensional quantum dots (2D QDs). As used herein, a "2D quantum dot" or "2D QD" refers to a semiconductor nanoparticle with a thickness of about 1-5 atomic or molecular monolayers and lateral dimensions that result in the nanoparticle being in the quantum confinement regime—i.e. the electronic properties of the nanoparticle differ from those of the bulk material. As may be appreciated, the lateral dimensions that provide a nanoparticle with electronic properties indicative of the quantum confinement regime may vary between nanoparticles of different compositions. In general, however, such lateral dimensions can be between 1 and 100 nm. As used herein, the term "2D nanosheet" is used to describe a particle having a thickness between 1 to 10 atomic or molecular monolayers, and wherein the lateral dimensions are sufficiently large that they extend beyond the quantum confinement regime. As used herein, a "single-layered quantum dot" or "single-layered QD" refers to a semiconductor nanoparticle whose thickness is a single monolayer and having lateral dimensions that result in the nanoparticle being in the quantum confinement regime. Compared with conventional zero-dimensional (0D) QDs, 2D QDs have a much higher surface area-to-volume ratio, which increases as the number of monolayers is decreased. The highest surface area-to-volume ratio is seen for single-layered QDs. This may lead to 2D QDs having very different surface chemistry from conventional QDs, which may be exploited for many applications. Thus far, the majority of research into 2D QDs has centered around layered materials, such as carbon-based materials (e.g. graphene and graphene oxide) and QDs of TMDCs, especially $MoS_2$, $MoSe_2$, $WS_2$ and $WSe_2$. However, more recently, there has been interest in the synthesis of 2D nanoparticles of conventional semiconductor materials such as II-VI semiconductors [E. Lhuillier et al., *Acc. Chem. Res.*, 2015, 48, 22; A. Riedinger et al., *Nat. Mater.*, 2017, 16, 743].

In some embodiments, the photodetector is a photodiode. A photodiode is typically based on a p-n junction. In a photodiode, when a photon of sufficient energy strikes the device, an electron-hole pair is created. If the absorption occurs in the junction's depletion region, or one diffusion length away from it, the built-in electric field of the depletion region leads to the carriers being swept from the junction, with holes moving towards the anode and electrons towards the cathode, producing a photocurrent.

In some embodiments, the photodetector is a photoconductor. A photoconductor is a device that detects a temporary change in conductivity of a semiconductor that results from illumination with light. Photons generate photo-excited carriers, which are extracted by an electric field generated by a voltage bias applied between the anode and cathode electrodes of the photodetector.

In some embodiments, the photodetector is a phototransistor having a base-collector junction. A phototransistor is similar to a photodiode, with the addition of a further n-type region. The phototransistor includes a photodiode with internal gain. It can be represented as a bipolar transistor enclosed in a transparent case such that photons can reach the base-collector junction. Electrons that are generated from photons in the base-collector junction are injected into the base, amplifying the current.

The three types of photodetectors each have different properties, and thus are useful in different applications. Phototransistors and photodiodes detect at a similar rate, but phototransistors have a slower response time (microseconds vs. nanoseconds for a photodiode). Phototransistors have a higher gain, while photodiodes exhibit less variation with temperature.

In at least one embodiment, a 2D QD-sensitized organic photodiode is employed. In at least one embodiment, a heterostructure photodetector comprising a 2D QD and a 2D nanosheet layer, i.e. with lateral dimensions considerably beyond the quantum confinement regime, is used. In at least one embodiment, a heterostructure photodetector comprising a first 2D QD layer and a second layer of 2D QDs of another material is used. In at least one embodiment, a heterostructure photodetector comprising a conventional QD layer and a 2D QD layer is used.

Figure 2:
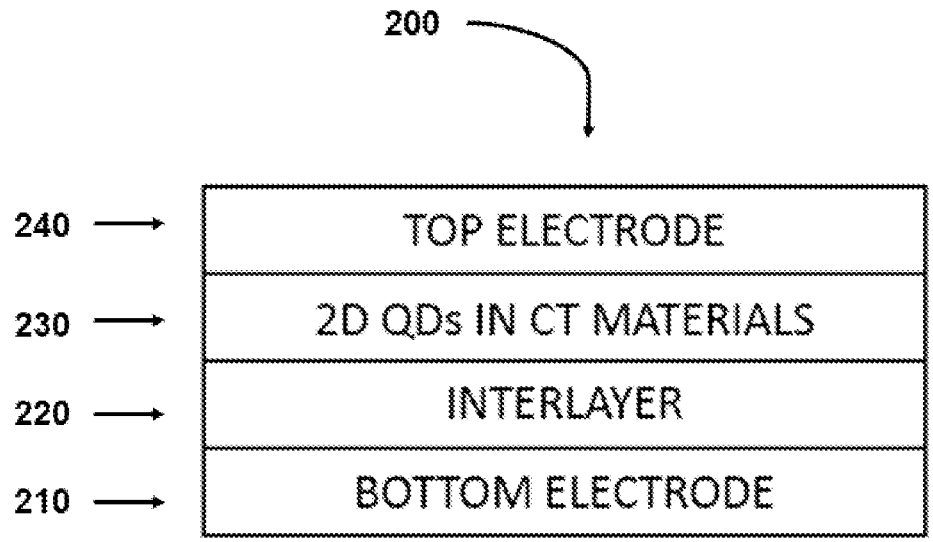
FIG. 2 is a schematic depiction of a photodetector device comprising 2D QDs within an organic photodiode in accordance with various aspects of the disclosure.

FIG. 2 is a schematic illustration of a photodetector 200 in accordance with various aspects of the disclosure. The photodetector 200 comprises a bottom electrode 210, an interlayer 220 disposed on the bottom electrode 210, a layer 230 comprising 2D QDs dispersed in a charge transport material disposed on the interlayer 220, and a top electrode 240 disposed on the 2D QD-containing layer 230. In the device configuration shown in FIG. 2, one or more of the top and bottom electrodes 210, 240 may be transparent to allow light to pass therethrough. The bottom electrode 210 may include a transparent conducting oxide, such as indium tin oxide (ITO), and aluminum-doped zinc oxide (AZO). The top electrode 240 may comprise one or more low-workfunction metals, such as aluminum, and silver.

The interlayer 220 serves to improve the electrical contact with the underlying bottom electrode 210. The interlayer 220 can be made of any suitable material such as, for example, poly(3,4-ethylenedioxythiophene) polystyrene sulfonate (PEDOT:PSS), $MoO_3$, and metal oxides having zinc, titanium, vanadium or nickel. The thickness of the interlayer 220 can range from about 1 nm to about 1000 nm, alternatively from about 10 nm to about 1000 nm, and alternatively from about 100 nm to about 1000 nm.

Shown schematically in FIG. 2, the layer 230, comprising 2D QDs dispersed in a charge transport material, may be produced by dispersing (by blending or mixing) 2D QDs in one or more organic charge transporting materials (electron- and/or hole-accepting and transporting organic materials) to form a heterojunction. Examples of suitable charge transporting materials include, but are not restricted to, [6,6]-phenyl-C61-butylic acid methyl ester (PCBM), poly(3-hexylthiophene) (P3HT), poly(N-octyldithieno [3,2-b:2'3'd]pyrrole-alt-5,6-bis(octyloxy)benzo[c][1,2,5]thiadiazole) (PDTPBT), poly[(9,9-dioctylfluorenyl-2,7-diyl-co(4,40-(N-4-sec-butylphenyl))diphenylamine)] (TFB), poly(N,N'-bis(4-butylphenyl)-N,N'-bis(phenyl)-benzidine) (poly-TPD), poly(-methoxy-5(2'-ethylhexyloxy)-1,4-phenylethlenevinylene) (MEH-PPV), poly(2,5-di(2'-ethylehexyloxy)-1,4-phenylenevinylene) (DEH-PPV), poly [2,6-(4,4'-bis(2-ethylhexyl)dithieno[3,2-b:2',3'-d]silole-alt-4,7(2,1,3-benzothiadiazole) (PSBTBT), poly[2,6-(4,4-bis(2-ethylhexyl)4H-cyclopenta[2,1-b;3,4-b']dithiophene)-alt-4,7-(2,1,3-benzothoadiazole)] (PCPDTBT), poly(2,3-didecyl-quinoxaline-5,8-diyl-alt-N-octyldithieno[3,2-b:2'3'-d] pyrrole) (PDTPQx), dithieno[3,2-b:2,3-d]pyrrole (DTP), poly(9,9-n-dihexyl-2,7-fluorenylenevinylene-alt-2,5-thienylenevinylene (PFT), ethoxylated polyethyleneimine (PEIE), 1-1-bis[(di-4-tolylamino phenyl]cyclohexane (TAPC), C60, multiwall carbon nanotubes, and other polymers, some of which the structures are shown in FIG. 1. In FIG. 1, the number average molar mass, $M_n$, for PDTPBT can range between about 17 kg $mol^{-1}$ and about 19 kg $mol^{-1}$. Also, in FIG. 1, the $M_n$ for PDBF can range between about 11 kg $mol^{-1}$ and about 13 kg $mol^{-1}$. Also, in FIG. 1, the $M_n$ for PDTD can range between about 30 kg $mol^{-1}$ and about 35 kg $mol^{-1}$. Also, in FIG. 1, the $M_n$ for PDTT can range between about 30 kg $mol^{-1}$ and about 35 kg $mol^{-1}$. Also, in FIG. 1, the $M_n$ for PDFT can range between about 35 kg $mol^{-1}$ and about 40 kg $mol^{-1}$. Also, in FIG. 1, the $M_n$ for PBDTTPD can range between about 10 kg $mol^{-1}$ and about 35 kg $mol^{-1}$. Also, in FIG. 1, the $M_n$ for PBDT-T8-TPD can range between about 35 kg $mol^{-1}$ and about 40 kg $mol^{-1}$. Also, in FIG. 1, the $M_n$ for P3HT can range between about 50 kg $mol^{-1}$ about 80 kg $mol^{-1}$. Finally, in FIG. 1, the $M_n$ for PBDT-T-FDP can range between about 50 kg $mol^{-1}$ and about 60 kg $mol^{-1}$.

Another material suitable for use as an organic material in a 2D-sensitized organic photodiode is spiro-OMeTAD, which may offer both UV detection and hole transporting properties (see Guo et al., *J. Mater. Chem. C*, 2018, 6, 2573). As discussed above, an interlayer, such as, but not restricted to, poly(3,4-ethylenedioxythiophene):poly(styrenesulphonate) (PEDOT:PSS), may be used to improve the electrical connection to the bottom contact. Alternative suitable materials may include solution-processable $MoO_3$ or $V_2O_x$ in the place of PEDOT.

In some instances, the 2D QD-containing layer 230 includes from about 10 vol % to about 95 vol % of the 2D QDs and from about 5 vol % to about 90 vol % of the one or more charge transport materials. In some instances, 2D QD-containing layer 230 includes from about 20 vol % to about 90 vol %, alternatively from about 30 vol % to about 85 vol %, alternatively from about 40 vol % to about 80 vol %, alternatively from about 50 vol % to about 75 vol %, and alternatively from about 60 vol % to about 70 vol % of the 2D QDs. In some instances, 2D QD-containing layer 230 includes from about 10 vol % to about 80 vol %, alternatively from about 15 vol % to about 70 vol %, alternatively from about 20 vol % to about 60 vol %, alternatively from about 25 vol % to about 50 vol %, and alternatively from about 30 vol % to about 40 vol % of the one or more charge transport materials.

The thickness of the 2D QD-containing layer 230 can range from about 10 nm to about 2 microns, alternatively from about 50 nm to about 1 micron, and alternatively from about 100 nm to about 750 nm, and alternatively from about 200 nm to about 500 nm.

Figure 3:
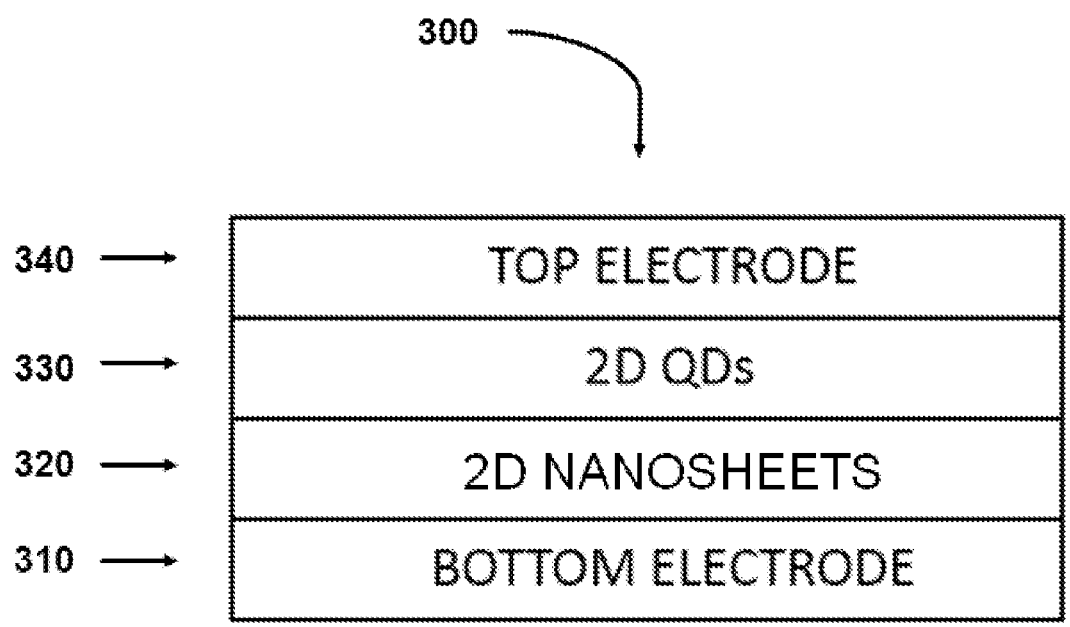
FIG. 3 is a schematic depiction of a heterostructure photodetector comprising a first layer of 2D QDs and a second layer of 2D nanosheets in accordance with various aspects of the disclosure.

FIG. 3 is a schematic depiction of a heterostructure photodetector 300 in accordance with various aspects of the disclosure. The heterostructure photodetector 300 comprises a bottom electrode 310, and first layer 320 having 2D nanosheets disposed on the bottom electrode 310, a second layer 330 having 2D QDs disposed on the 2D nanosheet-containing first layer 320, and a top electrode 340 disposed on the 2D QD-containing second layer 330. In this configuration, one or more of the top and bottom electrodes 310, 340 may be transparent to allow light to pass therethrough. To form a heterojunction, the 2D QDs and the 2D nanosheets in layers 320, 330 are chosen such that the conduction band and valence band of the 2D QDs is offset from the conduction band and valence band of the 2D nanosheets, to create a built-in electric field. This can be achieved either through selection of 2D QD and 2D nanosheet materials having different semiconductor band gaps, and/or tailoring of the lateral dimensions of the second 2D QDs and/or 2D nanosheets, and/or tailoring of the thickness of the 2D QDs and/or 2D nanosheets, and/or by functionalizing the surface of one or both of the 2D QDs and 2D nanosheets with different ligands that modify the band gaps of the materials. The junction width can control the wavelengths of light absorbed.

The thickness of each of the 2D nanosheet-containing layer 320 and the 2D QD-containing layer 330 can independently range from about 10 nm to about 1 micron, alternatively from about 25 nm to about 750 nm, alternatively from about 50 nm to about 500 nm, alternatively from about 75 nm to about 400 nm, and alternatively from about 100 nm to about 300 nm. Preferably, the combined thickness of the 2D nanosheet-containing layer 320 and the 2D QD-containing layer 330 is between about 50 nm and about 800 nm, more preferably between about 100 nm and about 700 nm, and even more preferably between about 200 nm and about 600 nm. In some instances, the 2D nanosheet-containing layer 320 and the 2D QD-containing layer 330 has the same or substantially the same thickness. In other instances, the 2D QD-containing layer 330 is thicker than the 2D nanosheet-containing layer 320. In other instances, the 2D nanosheet-containing layer 320 is thicker than the 2D QD-containing layer 330.

The 2D QD-containing layer 330 can be made to have a composition the same as, or substantially similar to 2D QD-containing layer 230. Like the 2D QD-containing layer 230, the 2D nanosheet-containing layer 320 from about 10 vol % to about 95 vol % of the 2D nanosheets and from about 5 vol % to about 90 vol % of the one or more charge transport materials. In some instances, 2D nanosheet-containing layer 320 includes from about 20 vol % to about 90 vol %, alternatively from about 30 vol % to about 85 vol %, alternatively from about 40 vol % to about 80 vol %, alternatively from about 50 vol % to about 75 vol %, and alternatively from about 60 vol % to about 70 vol % of the 2D nanosheets. In some instances, 2D nanosheet-containing layer 320 includes from about 10 vol % to about 80 vol %, alternatively from about 15 vol % to about 70 vol %, alternatively from about 20 vol % to about 60 vol %, alternatively from about 25 vol % to about 50 vol %, and alternatively from about 30 vol % to about 40 vol % of the one or more charge transport materials.

In some instances, the heterostructure photodetector 300 can further include an interlayer (not shown) disposed between the bottom electrode 310 and the 2D nanosheet-containing layer 320. The interlayer can be made of the same materials as interlayer 220 of photodetector 200. In FIG. 3, the 2D nanosheet-containing layer 320 and the 2D QD-containing layer 330 are shown as separate layers. In some instances, a transition layer (not shown) can be disposed between the 2D nanosheet-containing layer 320 and the 2D QD-containing layer 330, the transition layer having a combination of 2D nanosheets and 2D QDs. In some instances, the relative amounts of 2D nanosheets and 2D QDs can be uniform or substantially uniform throughout the thickness of the transition layer. In some instances, the transition layer can exhibit a gradient wherein the amount of 2D nanosheets decreases from the 2D nanosheet-containing layer 320 to the 2D QD-containing layer 330. In some instances, the transition layer can exhibit a gradient wherein the amount of 2D QDs increases from the 2D nanosheet-containing layer 320 to the 2D QD-containing layer 330.

Figure 4:
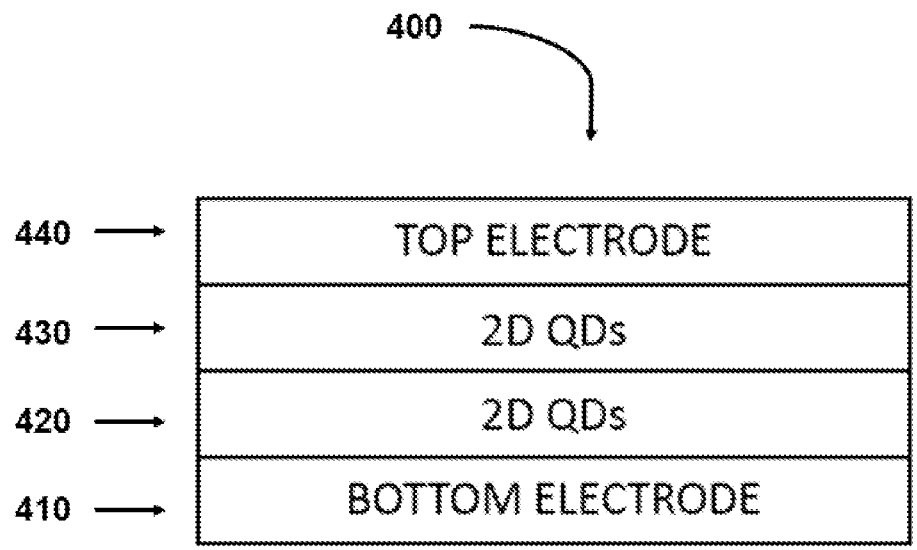
FIG. 4 is a schematic depiction of a heterostructure photodiode comprising a first layer of 2D QDs and a second layer of 2D QDs in accordance with various aspects of the disclosure.

FIG. 4 is a schematic depiction of another heterostructure photodetector 400 in accordance with various aspects of the disclosure. The heterostructure photodetector 400 comprises a bottom electrode 410, and first layer 420 having 2D QDs disposed on the bottom electrode 410, a second layer 430 having 2D QDs disposed on the 2D QD-containing first layer 420, and a top electrode 440 disposed on the 2D QD-containing second layer 430. In this configuration, one or more of the top and bottom electrodes 410, 420 may be transparent to allow light to enter into the device. To form a heterojunction, the 2D QDs of the first layer 420 and the 2D QDs of the second layer 430 are chosen such that the conduction band and the valence band of the 2D QDs in the first layer 420 are offset from the conduction band and valence band of the 2D QDs in the second layer 430. This can be achieved either through selection of first and second 2D QDs of materials having different semiconductor band gaps, and/or tailoring of the lateral dimensions of the first and second 2D QDs, and/or tailoring of the thickness of the first and second 2D QDs, and/or by functionalizing the surface of one or both of the first and second 2D QDs with different ligands that modify the band gaps of the materials. In some instances, the chemical composition of each of the first and second 2D QDs can be the same or substantially the same, but the first and second 2D QDs are differ in one or more of lateral dimensions, thicknesses and surface functionalization. The junction width can control the wavelengths of light absorbed.

The composition and/or thickness of each 2D QD-containing layer 420, 430 can be varied as described above for 2D QD-containing layer 230. Preferably, the combined thickness of the 2D QD-containing layers 420, 430 is between about 50 nm and about 800 nm, more preferably between about 100 nm and about 700 nm, and even more preferably between about 200 nm and about 600 nm. In some instances, each 2D QD-containing layer 420, 430 has the same or substantially the same thickness. In other instances, the 2D QD-containing layer 420 is thicker than the 2D QD-containing layer 430. In other instances, the 2D QD-containing layer 430 is thicker than the 2D QD-containing layer 420.

In some instances, the heterostructure photodetector 400 can further include an interlayer (not shown) disposed between the bottom electrode 410 and the 2D QD-containing layer 420. The interlayer can be made of the same materials as interlayer 220 of photodetector 200. In FIG. 4, the 2D QD-containing layer 420 and the 2D QD-containing layer 430 are shown as separate layers. In some instances, a transition layer (not shown) can be disposed between the 2D QD-containing layer 420 and the 2D QD-containing layer 430, the transition layer having a combination of first 2D QDs (i.e., the 2D QDs of layer 420) and second 2D QDs (i.e., the 2D QDs of layer 430). In some instances, the relative amounts of first 2D QDs and second 2D QDs can be uniform or substantially uniform throughout the thickness of the transition layer. In some instances, the transition layer can exhibit a gradient wherein the amount of first 2D QDs decreases from the 2D QD-containing layer 420 to the 2D QD-containing layer 430. In some instances, the transition layer can exhibit a gradient wherein the amount of second 2D QDs increases from the 2D QD-containing layer 420 to the 2D QD-containing layer 430.

Figure 5:
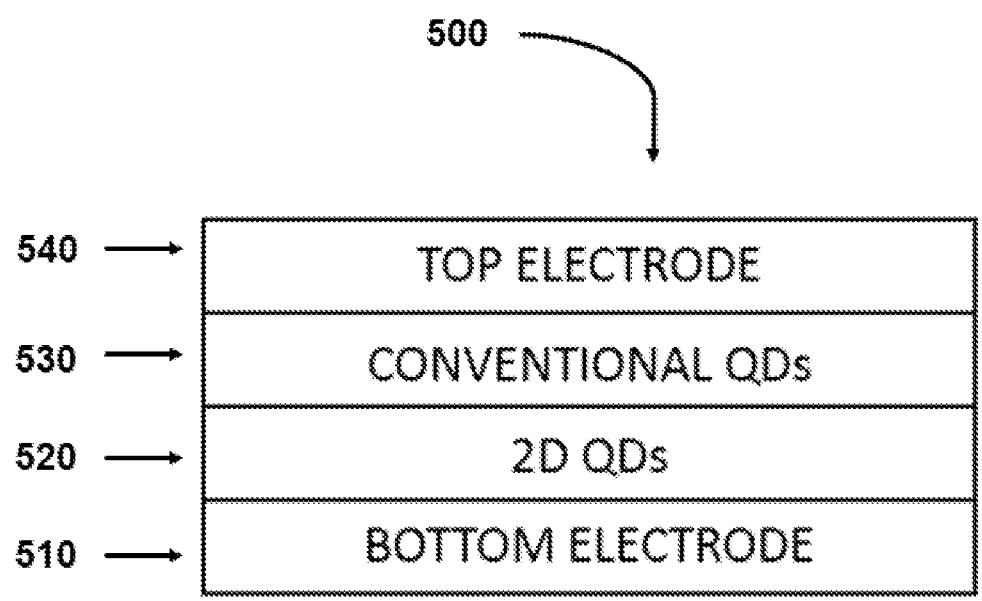
FIG. 5 is a schematic depiction of a heterostructure photodetector comprising a first layer of conventional QDs and a second layer of 2D QDs in accordance with various aspects of the disclosure.

FIG. 5 is a schematic depiction of yet another heterostructure photodetector 500 in accordance with various aspects of the disclosure. The heterostructure photodetector 500 comprises a bottom electrode 510, a first layer 520 having 2D QDs disposed on the bottom electrode 510, and a second layer 530 having conventional QDs disposed on the 2D QD-containing first layer 520, and a top electrode 540 disposed on the conventional QD-containing second layer 530. In this configuration, one or more of the top and bottom electrodes 510, 540 may be transparent to allow light to enter into the device. To form a heterojunction, the first 2D QD layer 520 and the second conventional QD layer 530 are chosen such that the conduction band and valence band of the first 2D QD layer is offset from the conduction band and valence band of the second conventional QD layer. This can be achieved either through selection of conventional QDs and 2D QDs of materials having different semiconductor band gaps, and/or tailoring of the diameter of the conventional QDs, and/or tailoring the lateral dimensions of the 2D QDs, and/or tailoring the thickness of the 2D QDs, and/or by functionalizing the surface one or both of the 2D QDs and conventional 2D QDs with different ligands that modify the band gaps of the materials. The junction width can control the wavelengths of light absorbed.

The 2D QD-containing layer 520 can be made to have a composition the same as, or substantially similar to 2D QD-containing layer 230. Like the 2D QD-containing layer 230, the 2D nanosheet-containing layer 520 from about 10 vol % to about 95 vol % of the 2D nanosheets and from about 5 vol % to about 90 vol % of the one or more charge transport materials. In some instances, conventional QD-containing layer 530 includes from about 20 vol % to about 90 vol %, alternatively from about 30 vol % to about 85 vol %, alternatively from about 40 vol % to about 80 vol %, alternatively from about 50 vol % to about 75 vol %, and alternatively from about 60 vol % to about 70 vol % of the conventional QDs. In some instances, conventional QD-containing layer 530 includes from about 10 vol % to about 80 vol %, alternatively from about 15 vol % to about 70 vol %, alternatively from about 20 vol % to about 60 vol %, alternatively from about 25 vol % to about 50 vol %, and alternatively from about 30 vol % to about 40 vol % of the one or more charge transport materials.

In some instances, the heterostructure photodetector 500 can further include an interlayer (not shown) disposed between the bottom electrode 510 and the 2D QD-containing layer 520. The interlayer can be made of the same materials as interlayer 220 of photodetector 200. In FIG. 5, the 2D QD-containing layer 520 and the conventional QD-containing layer 530 are shown as separate layers. In some instances, a transition layer (not shown) can be disposed between the 2D QD-containing layer 520 and the conventional QD-containing layer 530, the transition layer having a combination of 2D QDs (i.e., the 2D QDs of layer 520) and conventional QDs (i.e., the conventional QDs of layer 530). In some instances, the relative amounts of 2D QDs and conventional QDs can be uniform or substantially uniform throughout the thickness of the transition layer. In some instances, the transition layer can exhibit a gradient wherein the amount of 2D QDs decreases from the 2D QD-containing layer 520 to the conventional QD-containing layer 530. In some instances, the transition layer can exhibit a gradient wherein the amount of conventional QDs increases from the 2D QD-containing layer 520 to the conventional QD-containing layer 530.

Figure 6:
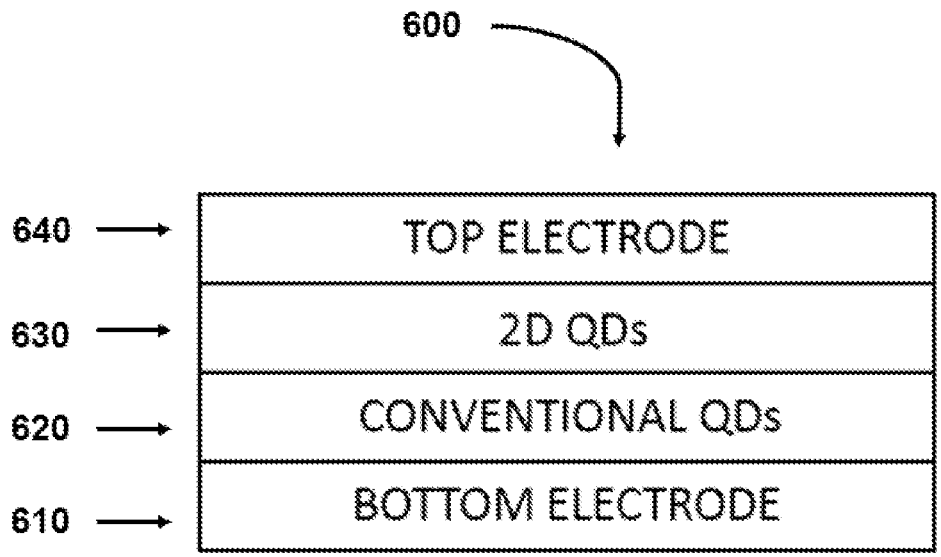
FIG. 6 is a schematic depiction of a heterostructure photodetector comprising a first layer of 2D QDs and a second layer of conventional QDs in accordance with various aspects of the disclosure.

FIG. 6 is a schematic depiction of yet another heterostructure photodetector 600 in accordance with various aspects of the disclosure. The heterostructure photodetector 600 comprises a bottom electrode 610, a first layer 620 having conventional QDs disposed on the bottom electrode 610, and a second layer 630 having 2D QDs disposed on the conventional QD-containing first layer 620, and a top electrode 640 disposed on the 2D QD-containing second layer 630. In this configuration, one or more of the top and bottom electrodes 610, 640 may be transparent to allow light to enter into the device. To form a heterojunction, the conventional QD-containing first layer 620 and the 2D QD-containing second layer 630 are chosen such that the conduction band and valence band of the conventional QDs are offset from the conduction band and valence band of the 2D QDs. This can be achieved either through selection of conventional QDs and 2D QDs of materials having different semiconductor band gaps, and/or tailoring of the diameter of the conventional QDs, and/or tailoring the lateral dimensions of the 2D QDs, and/or tailoring the thickness of the 2D QDs, and/or by functionalizing the surface one or both of the 2D QDs and conventional 2D QDs with different ligands that modify the band gaps of the materials. The junction width can control the wavelengths of light absorbed.

The composition and/or thickness of the conventional QD-containing layer 620 and the 2D QD-containing layer 630 can be varied as described above for the conventional QD-containing layer 520 and the 2D QD-containing layer 520, respectively. Preferably, the combined thickness of the conventional QD-containing layer 620 and the 2D QD-containing layer 630 is between about 50 nm and about 800 nm, more preferably between about 100 nm and about 700 nm, and even more preferably between about 200 nm and about 600 nm. In some instances, each of the conventional QD-containing layer 620 and the 2D QD-containing layer 630 has the same or substantially the same thickness. In other instances, the QD-containing layer 620 is thicker than the 2D QD-containing layer 630. In other instances, the 2D QD-containing layer 630 is thicker than the QD-containing layer 620.

In some instances, the heterostructure photodetector 600 can further include an interlayer (not shown) disposed between the bottom electrode 610 and the conventional QD-containing layer 620. The interlayer can be made of the same materials as interlayer 220 of photodetector 200. In FIG. 6, the conventional QD-containing layer 620 and the 2D QD-containing layer 630 are shown as separate layers. In some instances, a transition layer (not shown) can be disposed between the conventional QD-containing layer 620 and the 2D QD-containing layer 630, the transition layer having a combination of conventional QDs (i.e., the conventional QDs of layer 620) and 2D QDs (i.e., the 2D QDs of layer 630). In some instances, the relative amounts of conventional QDs and 2D QDs can be uniform or substantially uniform throughout the thickness of the transition layer. In some instances, the transition layer can exhibit a gradient wherein the amount of conventional QDs decreases from the conventional QD-containing layer 620 to the 2D QD-containing layer 630. In some instances, the transition layer can exhibit a gradient wherein the amount of 2D QDs increases from the conventional QD-containing layer 620 to the 2D QD-containing layer 630.

Figure 7:
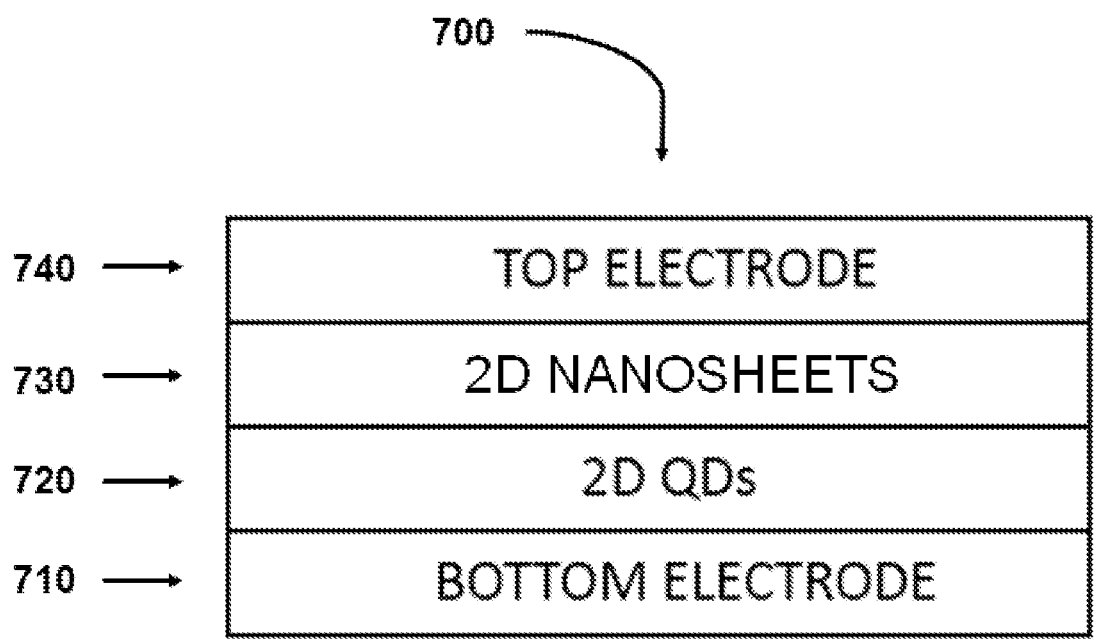
FIG. 7 is a schematic depiction of a heterostructure photodetector comprising a first layer of 2D nanosheets and a second layer of 2D QDs in accordance with various aspects of the disclosure.

FIG. 7 is a schematic depiction of a heterostructure photodetector 700 in accordance with various aspects of the disclosure. The heterostructure photodetector 700 comprises a bottom electrode 710, and first layer 720 having 2D QDs disposed on the bottom electrode 710, a second layer 730 having 2D nanosheets disposed on the 2D QD-containing first layer 720, and a top electrode 740 disposed on the 2D nanosheet-containing second layer 730. In this configuration, one or more of the top and bottom electrodes 710, 740 may be transparent to allow light to enter into the device. To form a heterojunction, the 2D QDs and the 2D nanosheets in layers 720, 730 are chosen such that the conduction band and valence band of the 2D QDs is offset from the conduction band and valence band of the 2D nanosheets, to create a built-in electric field. This can be achieved either through selection of 2D QD and 2D nanosheet materials having different semiconductor band gaps, and/or tailoring of the lateral dimensions of the second 2D QDs and/or 2D nanosheets, and/or tailoring of the thickness of the 2D QDs and/or 2D nanosheets, and/or by functionalizing the surface of one or both of the 2D QDs and 2D nanosheets with different ligands that modify the band gaps of the materials. The junction width can control the wavelengths of light absorbed.

The composition and/or thickness of the 2D QD-containing layer 720 and the 2D nanosheet-containing layer 730 can be varied as described above for the 2D QD-containing layer 330 and the 2D nanosheet-containing layer 320, respectively. Preferably, the combined thickness of the 2D QD-containing layer 720 and the 2D nanosheet-containing layer 730 is between about 50 nm and about 800 nm, more preferably between about 100 nm and about 700 nm, and even more preferably between about 200 nm and about 600 nm. In some instances, each of the 2D QD-containing layer 720 and the 2D nanosheet-containing layer 730 has the same or substantially the same thickness. In other instances, the 2D QD-containing layer 720 is thicker than the 2D nanosheet-containing layer 730. In other instances, the 2D nanosheet-containing layer 730 is thicker than the 2D QD-containing layer 720.

In some instances, the heterostructure photodetector 700 can further include an interlayer (not shown) disposed between the bottom electrode 710 and the 2D QD-containing layer 720. The interlayer can be made of the same materials as interlayer 220 of photodetector 200. In FIG. 7, the 2D QD-containing layer 720 and the 2D nanosheet-containing layer 730 are shown as separate layers. In some instances, a transition layer (not shown) can be disposed between the 2D QD-containing layer 720 and the 2D nanosheet-containing layer 730, the transition layer having a combination of 2D QDs (i.e., the 2D QDs of layer 720) and 2D nanosheets (i.e., the 2D nanosheets of layer 730). In some instances, the relative amounts of 2D QDs and 2D nanosheets can be uniform or substantially uniform throughout the thickness of the transition layer. In some instances, the transition layer can exhibit a gradient wherein the amount of 2D QDs decreases from the 2D QD-containing layer 720 to the 2D nanosheet-containing layer 730. In some instances, the transition layer can exhibit a gradient wherein the amount of 2D nanosheets increases from the 2D QD-containing layer 720 to the 2D nanosheet-containing layer 730.

2D QDs in accordance with various aspects of the disclosure may be synthesized colloidally and deposited via solution processing. Suitable 2D QD materials include, but are not restricted to:

graphene, graphene oxide and reduced graphene oxide;

TMDCs such as, for example, $WO_2$; $WS_2$; $WSe_2$; $WTe_2$; $MnO_2$; $MoO_2$; $MoS_2$; $MoSe_2$; $MoTe_2$; $NiO_2$; $NiTe_2$; $NiSe_2$; $VO_2$; $VS_2$; $VSe_2$; $TaS_2$; $TaSe_2$; $RuO_2$; $RhTe_2$; $PdTe_2$; $HfS_2$; $NbS_2$; $NbSe_2$; $NbTe_2$; $FeS_2$; $TiO_2$; $TiS_2$; $TiSe_2$; and $ZrS_2$;

transition metal trichalcogenides such as, for example, $TaO_3$; $MnO_3$; $WO_3$; $ZrS_3$; $ZrSe_3$; $HfS_3$; and $HfSe_3$;

Group 13-16 (III-VI) compounds such as, for example, InS; InSe; GaS; GaSe; and GaTe;

Group 15-16 (IV-VI) compounds such as, for example, $Bi_2Se_3$; and $Bi_2Te_3$;

nitrides such as, for example, h-BN;

oxides such as, for example, $LaVO_3$; $LaMnO_3$; $V_2O_5$; $LaNbO_7$; $Ca_2Nb_3O_{10}$; $Ni(OH)_2$; and $Eu(OH)_2$; layered copper oxides; micas; and bismuth strontium calcium copper oxide (BSCCO);

phosphides such as, for example, $Li_7MnP_4$; and $MnP_4$; and 2D allotropes of Group 14 elements such as, for example, silicene; germanene; and stanene.

Within the aforementioned materials, adjacent layers are held together by van der Waals interactions, which can readily be broken by techniques such as exfoliation techniques, for example, liquid phase exfoliation (LPE) to form 2D flakes. In alternative embodiments, the 2D QDs may comprise semiconductor materials that are not traditionally layered, including, but not restricted to:

Group 12-16 (II-VI) semiconductors such as, for example, ZnS; ZnSe; CdS; CdSe; CdTe;

Group 13-15 (III-V) materials such as, for example, AN, AlP, AlAs, GaN; GaP; GaAs; InN; InP; InAs;

Group 15-16 (V-VI) materials such as, for example, PbS, PbSe, PbTe; and

Group materials such as, for example, $CuGaS_2$; $CuGaSe_2$; $CuGa(S,Se)_2$; $CuInS_2$, $CuInSe_2$; $CuIn(S,Se)_2$; $Cu(In,Ga)S_2$; $Cu(In,Ga)Se_2$; $Cu(In,Ga)(S,Se)_2$; $CuInTe_2$; $AgInS_2$; and $AgInSe_2$ including doped species and alloys thereof.

The 2D QDs of the aforementioned materials may be formed, for example, via a physical or chemical cutting process. Specifically, zero-dimensional (0D), one-dimensional (1D) or three-dimensional (3D) of a desired shape, size and composition mat be formed, followed by treatment, such as chemical treatment, e.g. reflux, LPE and reflux, or intercalation and exfoliation, to form 2D QDs of uniform size as dictated by the intrinsic shape of the 3D or OD nanoparticles. The process is scalable and can be used to produce 2D QDs with uniform properties in large volumes. As used herein, the "cutting" of a nanoparticle means the separation of the nanoparticle into two or more parts. The term is not intended to imply any restriction on the method of separation, and can include physical and chemical methods of separation. Physical separation methods may include, but are not restricted to: mechanical exfoliation (the so-called "Scotch tape method"), delamination, grinding, and milling. As used herein, the "chemical cutting" of a nanoparticle means the separation of the nanoparticle into two or more parts, wherein the separation is effected by a chemical treatment. In certain embodiments, a chemical treatment may include: the application of heat, pressure, vacuum, ultrasonication, and/or agitation to a solution or dispersion of nanoparticles; chemical etching; and intercalation. Non-limiting examples of chemical cutting methods include: refluxing the nanoparticles in solution; LPE of the nanoparticles followed by reflux; or intercalation and exfoliation of the nanoparticles.

The cutting of the 0D, 1D or 3D nanoparticles into 2D QDs can be performed using any suitable technique. Suitable examples include chemical and physical exfoliation processes. In one embodiment, the cutting of the prefabricated nanoparticles is performed by a chemical method, such as LPE, which comprises the ultrasonication of the prefabricated nanoparticles in a solvent. The surface tension of the solvent may be chosen to match that of the material being exfoliated. In some embodiments, the exfoliated nanoparticles are subsequently refluxed in solution.

In some embodiments, the cutting of 0D, 1D or 3D nanoparticles may be carried out by refluxing the prefabricated nanoparticles in solution without prior exfoliation. One of ordinary skill in the art will recognize that the temperature at which the 0D, 1D or 3D nanoparticle solution is refluxed will depend on the boiling point of the solvent in which the solution is formed. Without wishing to be bound by any particular theory, one possible mechanism is that the application of heat may thermally expand the layers within the 0D, 1D or 3D nanoparticles; refluxing the solution may form a gas which chemically cuts the layers apart. In some embodiments, the solution comprises a coordinating solvent. Examples of suitable coordinating solvents include, but are not restricted to: saturated alkyl amines such as, for example, $C_6$-$C_{50}$ alkyl amines; unsaturated fatty amines such as, for example, oleylamine; fatty acids such as, for example, myristic acid, palmitic acid, and oleic acid; phosphines such as, for example, trioctylphosphine (TOP); phosphine oxides such as, for example, trioctylphosphine oxide (TOPO); alcohols such as, for example hexadecanol, benzylalcohol, ethylene glycol, propylene glycol; and may include primary, secondary, tertiary and branched solvents. In some embodiments, the solution comprises a non-coordinating solvent, such as, but not restricted to, a $C_{11}$-$C_{50}$ alkane. In some embodiments, the boiling point of the solvent is between 150° C. to 600° C., for example, 160° C. to 400° C., or more particularly 180° C. to 360° C. In a particular embodiment, the solvent is hexadecylamine.

In yet further embodiments, the cutting of prefabricated nanoparticles is performed by an intercalation and exfoliation process. Intercalation and exfoliation of TMDC multi-layered nanostructures can be accomplished using Lewis base intercalates. A first intercalation and exfoliation process may be carried out by stirring the prefabricated nanoparticles in a first solvent in the presence of a first intercalating agent and a second intercalating agent for a first time period. Optionally, a second solvent may subsequently be added, followed by stirring for a second time period. In some embodiments, a second intercalation and exfoliation process is carried out by mixing the product of a first intercalation and exfoliation process with a third intercalating agent and a third solvent and stirring for a third time period. Optionally, a fourth solvent may subsequently be added, followed by stirring for a fourth time period. The first intercalating agent and the second intercalating agent may comprise hydrocarbons wherein the hydrocarbon chain length of the first intercalating agent is different to the hydrocarbon chain length of the second intercalating agent. The third intercalating agent may be the same or different from the first and/or second intercalating agent. Suitable first, second and third intercalating agents may include, but are not restricted to:

Lewis bases, such as amines such as, for example, propylamine, hexylamine; alkoxides such as, for example, sodium methoxide, sodium ethoxide; carboxylates such as, for example, sodium hexanoate; and amino alcohols such as, for example, 3-amino-1-propanol;

aminothiols such as, for example, cysteamine, 6-amino-1-hexanethiol, and 8-amino-1-octanethiol;

amino acids, including alkyl amino acids, such as, for example, 3-aminopropanoic acid (β-alanine), 6-aminohexanoic acid, 8-aminooctanoic acid; and metal salts such as, for example, those having the general formula $MX_n$ where M is Mo, Cd, Zn, or In, and X is a halide (especially $Cl^-$, $Br^-$, and $I^-$), acetate, caprylate, palimatate, laurate, myristate or oleate. Another suitable metal salt is $[MoCl_5]_2$.

Generally, the choice of solvent(s) in which the intercalation and exfoliation process is carried out will depend on the choice of nanoparticles and intercalating agents. During intercalation and exfoliation, it is desirable that the nanoparticles are well dispersed or dissolved in the solvent(s). It is further desirable that the intercalating agent(s) are soluble in the solvent(s). The second solvent may be different from the first solvent. The third solvent may be the same as the first solvent or the second solvent, or may be different from both the first solvent and the second solvent. In some instances, suitable solvents include polar aprotic solvents such as, for example, dimethyl sulfoxide (DMSO), N-methylformamide (NMF) and acetonitrile. In some instances, suitable solvents include polar protic solvents such as, for example, propanol and isopropanol.

The first time period may range from about 1 hour to about 1 month, alternatively from about 2 hours to about 2 weeks, and alternatively from about 4 hours to about 3 days. The second time period may range from about 1 hour to about 2 months, alternatively from about 2 days to about 2 weeks, and alternatively from about 1 week to about 3 weeks. The third time period may range from about 1 hour to about 1 month, alternatively from about 2 hours to about 2 weeks, and alternatively from about 4 hours to about 3 days. The fourth time period may range from about 1 hour to about 2 months, alternatively from about 2 days to about 2 weeks, and alternatively from about 1 week to about 3 weeks. Generally, the time period will depend on factors such as the choice of solvent(s) and intercalating agent(s), the strength of the bonding within the nanoparticles, and the concentration of nanoparticles to intercalating agents in solution, and that a longer time period may lead to a higher yield of 2D nanoflakes.

In some embodiments, the first and/or second and/or subsequent intercalation and exfoliation processes may be effected using ultrasonication. Using ultrasonication in the place of stirring may facilitate a reduction in the time period(s) required to effect the chemical cutting process.

Other cutting techniques can be used for the cutting of the 0D, 1D or 3D nanoparticles to 2D QDs, such as, but not restricted to, etching techniques. According to certain embodiments, the 2D QDs may then be isolated from solution by techniques such as, but not limited to: centrifugation; filtration; dialysis or column chromatography. The resulting 2D nanoflakes may be dispersed in a solvent to form an ink that may be deposited to form a thin film using conventional solution-based deposition techniques such as, but not restricted to: drop-casting, spin-coating, slit coating, spray coating, slot dye coating, inkjet printing or doctor blading. Inherent uniformity in the properties of the 2D QDs may result in a high degree of uniformity in the resulting thin film. The film thickness may be controlled by, for example, altering the concentration of the ink and/or by changing the size of the 2D QDs.

Layers of 2D nanosheets may be formed using techniques, such as, but not restricted to, mechanical exfoliation, chemical vapor deposition (CVD), atomic layer deposition (ALD); molecular beam epitaxy (MBE); lateral heteroepitaxy; and vapor-solid growth. Suitable 2D nanosheets for 2D nanosheet-containing layers include, but are not restricted to:

graphene, graphene oxide and reduced graphene oxide;

TMDCs such as, for example, $WO_2$; $WS_2$; $WSe_2$; $WTe_2$; $MnO_2$; $MoO_2$; $MoS_2$; $MoSe_2$; $MoTe_2$; $NiO_2$; $NiTe_2$; $NiSe_2$; $VO_2$; $VS_2$; $VSe_2$; $TaS_2$; $TaSe_2$; $RuO_2$; $RhTe_2$; $PdTe_2$; $HfS_2$; $NbS_2$; $NbSe_2$; $NbTe_2$; $FeS_2$; $TiO_2$; $TiS_2$; $TiSe_2$; and $ZrS_2$;

transition metal trichalcogenides such as, for example, $TaO_3$; $MnO_3$; $WO_3$; $ZrS_3$; $ZrSe_3$; $HfS_3$; and $HfSe_3$;

Group 13-16 (III-VI) compounds such as, for example, InS; InSe; GaS; GaSe; and GaTe;

Group 15-16 (IV-VI) compounds such as, for example, $Bi_2Se_3$; and $Bi_2Te_3$;

nitrides such as, for example, h-BN;

oxides such as, for example, $LaVO_3$; $LaMnO_3$; $V_2O_5$; $LaNbO_7$; $Ca_2Nb_3O_{10}$; $Ni(OH)_2$; and $Eu(OH)_2$; layered copper oxides; micas; and BSCCO;

phosphides such as, for example, $Li_7MnP_4$; and $MnP_4$; and 2D allotropes of Group 14 elements such as, for example, silicene; germanene; and stanene.

For devices containing a layer of conventional QDs, the QD layer may be formed from materials including, but not restricted to:

IIA-VIB (2-16) material, consisting of a first element from group 2 of the periodic table and a second element from group 16 of the periodic table and also including ternary and quaternary materials and doped materials. Nanoparticle material includes but is not restricted to: MgS, MgSe, MgTe, CaS, CaSe, CaTe, SrS, SrSe, SrTe, BaS, BaSe, BaTe;

IIB-VIB (12-16) material consisting of a first element from group 12 of the periodic table and a second element from group 16 of the periodic table and also including ternary and quaternary materials and doped materials. Nanoparticle material includes but is not restricted to: ZnS, ZnSe, ZnTe, CdS, CdSe, CdTe, HgS, HgSe, HgTe;

II-V material, consisting of a first element from group 12 of the periodic table and a second element from group 15 of the periodic table and also including ternary and quaternary materials and doped materials. Nanoparticle material includes but is not restricted to: $Zn_3P_2$, $Zn_3As_2$, $Cd_3P_2$, $Cd_3As_2$, $Cd_3N_2$, $Zn_3N_2$;

III-V material, consisting of a first element from group 13 of the periodic table and a second element from group 15 of the periodic table and also including ternary and quaternary materials and doped materials. Nanoparticle material includes but is not restricted to: BP, AlP, AlAs, AlSb; GaN, GaP, GaAs, GaSb; InN, InP, InAs, InSb, AlN, BN;

III-IV material, consisting of a first element from group 13 of the periodic table and a second element from group 14 of the periodic table and also including ternary and quaternary materials and doped materials. Nanoparticle material includes but is not restricted to: $B_4C$, $Al_4C_3$, $Ga_4C$;

III-VI material, consisting of a first element from group 13 of the periodic table and a second element from group 16 of the periodic table and also including ternary and quaternary materials. Nanoparticle material includes but is not restricted to: $Al_2S_3$, $Al_2Se_3$, $Al_2Te_3$, $Ga_2S_3$, $Ga_2Se_3$, GeTe; $In_2S_3$, $In_2Se_3$, $Ga_2Te_3$, $In_2Te_3$, InTe;

IV-VI material, consisting of a first element from group 14 of the periodic table and a second element from group 16 of the periodic table, and also including ternary and quaternary materials and doped materials. Nanoparticle material includes but is not restricted to: PbS, PbSe, PbTe, SnS, SnSe, SnTe;

V-VI material, consisting of a first element from group 15 of the periodic table and a second element from group 16 of the periodic table, and also including ternary and quaternary materials and doped materials. Nanoparticle material includes but is not restricted to: $Bi_2Te_3$, $Bi_2Se_3$, $Sb_2Se_3$, $Sb_2Te_3$; and Nanoparticle material, consisting of a first element from any group in the transition metal of the periodic table, and a second element from group 16 of the periodic table and also including ternary and quaternary materials and doped materials. Nanoparticle material includes but is not restricted to: NiS, CrS, $CuInS_2$, $AgInS_2$.

In some instances, in heterostructure devices according to various aspects of the disclosure, the relative band gaps of the semiconductor materials may be selected to form a Type I heterostructure, for example $WSe_2$ 2D QDs with a layer of $MoTe_2$ 2D QDs or a $MoTe_2$ 2D nanosheet layer. In some instances, the relative band gaps of the semiconductor materials may be chosen to form a Type II heterostructure, for example PbS QDs with a $WSe_2$ 2D QD layer, or $MoS_2$ 2D QDs with either a layer $WSe_2$ 2D QDs or a $WSe_2$ 2D nanosheet layer.

In some instances, one or more of the 2D layers may be a single monolayer in thickness. Making the sensitizer as thin as possible may be advantageous to maximize the charge screening effect, flexibility and device transparency. Thickness approaching the absorption depth may be desirable to maximize the absorption of incoming light. However, thicker devices may also be desirable for stronger absorption. Tuning the thickness of the material also provides a means to control its band gap. Therefore, in some instances, one or more of the 2D layers may be between 1-5 monolayers. In some instances, the 2D nanosheet layers may be a monolayer. Monolayers may provide advantageous properties over few-layer or bulk material. For example, transition metal dichalcogenides display a transition from an indirect to a direct band gap upon monolayer formation.

A number of strategies may be implemented to enhance the charge transport within the 2D QD layer. For example, the inherent 2D QD ligands may be replaced with shorter chain ligands. As used herein, a "short-chain ligand" refers to a ligand having a hydrocarbon chain of eight carbons or fewer. Examples of suitable short-chain ligands include, but are not restricted to: alkane thiols such as 1-octanethiol, 1-heptanethiol, 1-hexanethiol, 1-pentanethiol, 1-butanethiol, 1-propanethiol; alkylamines such as methylamine, ethylamine, propylamine, butylamine, octylamine, allylamine; and carboxylic acids such as octanoic acid, heptanoic acid, hexanoic acid, pentanoic acid, butanoic acid, and propanoic acid. Other suitable ligands may include pyridines and pyrrolidones. In some instances, bridging ligands may be used to improve the connectivity between adjacent 2D QDs. Suitable examples include, but are not restricted to, bidentate ligands such as ethanedithiol or 3-mercaptopropionic acid.

A further strategy to improve the connectivity between 2D QDs may include the use of chalcogen ligands. In this method, QDs may be "necked" by removing the organic surface ligands and passivating the QD surface with chalcogen ligands. In some instances, adjacent QDs may be fused. Using fused 2D QDs, a film may be formed, wherein the 2D QDs include ligands on portions of their outer surface that have not been fused. Fusing may lead to the 2D QDs substantially maintaining their individual properties while being joined by regions through which current can readily flow. In one embodiment, as-synthesized 2D QDs may be subjected to ligand exchange, to replace the inherent ligands with shorter, more volatile ligands. The ligand-exchanged 2D QDs may then be solution deposited, then the short-chain ligands removed to bring the 2D QDs into close proximity so that some of the 2D QDs contact their neighbors. This is known as "necking". The necked 2D QDs may subsequently be annealed to fuse the 2D QDs together. In general, fused 2D QDs, and the connection between them, will not contain defect states, which enables current to flow readily between them.

When conventional QDs are used, such as in the conventional QD-containing layer 530 of photodetector 500 or the conventional QD-containing layer 620 of photodetector 600, the conventional QDs can be core, core-shell or core-multishell QDs having sizes ranging from 2-100 nm. The material of the core can comprise:

- IIA-VIA (2-16) material, consisting of a first element from group 2 of the periodic table and a second element from group 16 of the periodic table and also including ternary and quaternary materials and doped materials. Nanoparticle material includes but is not restricted to: MgS, MgSe, MgTe, CaS, CaSe, CaTe, SrS, SrSe, SrTe, BaS, BaSe, BaTe;
- IIB-VIA (12-16) material consisting of a first element from group 12 of the periodic table and a second element from group 16 of the periodic table and also including ternary and quaternary materials and doped materials. Nanoparticle material includes but is not restricted to: ZnO, ZnS, ZnSe, ZnTe, CdS, CdSe, CdTe, HgS, HgSe, HgTe;
- II-V material consisting of a first element from group 12 of the periodic table and a second element from group 15 of the periodic table and also including ternary and quaternary materials and doped materials. Nanoparticle material includes but is not restricted to: $Zn_3P_2$, $Zn_3As_2$, $Cd_3P_2$, $Cd_3As_2$, $Cd_3N_2$, $Zn_3N_2$;
- III-V material consisting of a first element from group 13 of the periodic table and a second element from group 15 of the periodic table and also including ternary and quaternary materials and doped materials. Nanoparticle material includes but is not restricted to: BP, AlP, AlAs, AlSb; GaN, GaP, GaAs, GaSb; InN, InP, InAs, InSb, AlN, BN;
- III-IV material consisting of a first element from group 13 of the periodic table and a second element from group 14 of the periodic table and also including ternary and quaternary materials and doped materials. Nanoparticle material includes but is not restricted to: $B_4C$, $Al_4C_3$, $Ga_4C$;
- III-VI material consisting of a first element from group 13 of the periodic table and a second element from group 16 of the periodic table and also including ternary and quaternary materials. Nanoparticle material includes but is not restricted to: $Al_2S_3$, $Al_2Se_3$, $Al_2Te_3$, $Ga_2S_3$, $Ga_2Se_3$, GeTe; $In_2S_3$, $In_2Se_3$, $Ga_2Te_3$, $In_2Te_3$, InTe;
- IV-VI material consisting of a first element from group 14 of the periodic table and a second element from group 16 of the periodic table, and also including ternary and quaternary materials and doped materials. Nanoparticle material includes but is not restricted to: PbS, PbSe, PbTe, SnS, SnSe, SnTe;
- V-VI material consisting of a first element from group 15 of the periodic table and a second element from group 16 of the periodic table, and also including ternary and quaternary materials and doped materials. Nanoparticle material includes but is not restricted to: $Bi_2Te_3$, $Bi_2Se_3$, $Sb_2Se_3$, $Sb_2Te_3$; and Nanoparticle material consisting of a first element from any group in the transition metal of the periodic table, and a second element from group 16 of the periodic table and also including ternary and quaternary materials and doped materials. Nanoparticle material includes but is not restricted to: NiS, CrS, $CuInS_2$, $AgInS_2$.

By the term doped nanoparticle for the purposes of specifications and claims, refer to nanoparticles of the above and a dopant comprised of one or more main group or rare earth elements, this most often is a transition metal or rare earth element, such as but not limited to zinc sulfide with manganese, such as ZnS nanoparticles doped with $Mn^+$.

The term "ternary material," for the purposes of specifications and claims, refers to QDs of the above but a three component material. The three components are usually compositions of elements from the as mentioned groups Example being $(Zn_xCd_{x-1}S)_mL_n$ nanocrystal (where L is a capping agent).

The term "quaternary material," for the purposes of specifications and claims, refer to nanoparticles of the above but a four-component material. The four components are usually compositions of elements from the as mentioned groups Example being $(Zn_xCd_{x-1}S_ySe_{y-1})_mL_n$ nanocrystal (where L is a capping agent).

The material used on any shell or subsequent numbers of shells grown onto the conventional QD core in most cases will be of a similar lattice type material to the core material i.e. have close lattice match to the core material so that it can be epitaxially grown on to the core, but is not necessarily restricted to materials of this compatibility. The material used on any shell or subsequent numbers of shells grown on to the core present in most cases will have a wider bandgap then the core material but is not necessarily restricted to materials of this compatibility. The materials of any shell or subsequent numbers of shells grown on to the core can include material comprising:

- IIA-VIA (2-16) material, consisting of a first element from group 2 of the periodic table and a second element from group 16 of the periodic table and also including ternary and quaternary materials and doped materials. Nanoparticle material includes but is not restricted to: MgS, MgSe, MgTe, CaS, CaSe, CaTe, SrS, SrSe, SrTe;
- IIB-VIA (12-16) material consisting of a first element from group 12 of the periodic table and a second element from group 16 of the periodic table and also including ternary and quaternary materials and doped materials. Nanoparticle material includes but is not restricted to: ZnS, ZnSe, ZnTe, CdS, CdSe, CdTe, HgS, HgSe, HgTe;
- II-V material consisting of a first element from group 12 of the periodic table and a second element from group 15 of the periodic table and also including ternary and quaternary materials and doped materials. Nanoparticle material includes but is not restricted to: $Zn_3P_2$, $Zn_3As_2$, $Cd_3P_2$, $Cd_3As_2$, $Cd_3N_2$, $Zn_3N_2$;
- III-V material consisting of a first element from group 13 of the periodic table and a second element from group 15 of the periodic table and also including ternary and quaternary materials and doped materials. Nanoparticle material includes but is not restricted to: BP, AlP, AlAs, AlSb; GaN, GaP, GaAs, GaSb; InN, InP, InAs, InSb, AlN, BN;
- III-IV material consisting of a first element from group 13 of the periodic table and a second element from group 14 of the periodic table and also including ternary and quaternary materials and doped materials. Nanoparticle material includes but is not restricted to: $B_4C$, $Al_4C_3$, $Ga_4C$;
- III-VI material consisting of a first element from group 13 of the periodic table and a second element from group 16 of the periodic table and also including ternary and quaternary materials. Nanoparticle material includes but is not restricted to: $Al_2S_3$, $Al_2Se_3$, $Al_2Te_3$, $Ga_2S_3$, $Ga_2Se_3$, $In_2S_3$, $In_2Se_3$, $Ga_2Te_3$, $In_2Te_3$;
- IV-VI material consisting of a first element from group 14 of the periodic table and a second element from group 16 of the periodic table and also including ternary and quaternary materials and doped materials. Nanoparticle material includes but is not restricted to: PbS, PbSe, PbTe, SnS, SnSe, SnTe;

V-VI material consisting of a first element from group 15 of the periodic table and a second element from group 16 of the periodic table, and also including ternary and quaternary materials and doped materials. Nanoparticle material includes but is not restricted to: $Bi_2Te_3$, $Bi_2Se_3$, $Sb_2Se_3$, $Sb_2Te_3$; and Nanoparticle material consisting of a first element from any group in the transition metal of the periodic table, and a second element from group 16 of the periodic table and also including ternary and quaternary materials and doped materials. Nanoparticle material includes but is not restricted to: NiS, CrS, $CuInS_2$, $AgInS_2$.

The aforementioned strategies for increasing the connectivity within the 2D QD layer may also be applied to a conventional QD layer.

Photodetector devices in accordance with various aspects of the present disclosure may be integrated with complementary metal-oxide-semiconductor (CMOS) circuitry. Devices comprising 2D QDs may be fabricated using CMOS techniques, for example by spin-coating a 2D QD layer onto a prefabricated CMOS electronic read-out circuit. Integration into CMOS circuitry may be desirable to form small pixels, to enable high resolution sensors.

In some instances, a number of pixels that have spectral sensitivity in different regions may be monolithically integrated. The spectral sensitivity of each pixel may be tuned by modifying the lateral dimensions and/or thickness of the 2D QDs.

In some instances, a phototransistor device in accordance with various aspects of the present disclosure may be gated. Gating acts as a control mechanism and allows increased functionality as the gate voltage can be varied to act as either a switch or as an amplifier. In particular, the high carrier mobility of 2D materials may be advantageous as the gain is directly proportional to the carrier mobility.

The foregoing presents particular embodiments embodying the principles of the invention. Those skilled in the art will be able to devise alternatives and variations which, even if not explicitly disclosed herein, embody those principles and are thus within the scope of the invention. Although particular embodiments of the present invention have been shown and described, they are not intended to limit what this patent covers. One skilled in the art will understand that various changes and modifications may be made without departing from the scope of the present invention as literally and equivalently covered by the following claims.

What is claimed is:

1. A heterostructure photodetector comprising:
a first electrode;
a first photoabsorbing layer comprising a first photoabsorbing material;
an interlayer disposed between the first electrode and the first photoabsorbing layer, wherein
the interlayer is made of a metal oxide having zinc, titanium, vanadium or nickel, and
the interlayer has a thickness ranging from about 100 nm to about 1000 nm;
a second photoabsorbing layer disposed on the first photoabsorbing layer, the second photoabsorbing layer comprising a second photoabsorbing material; and
a second electrode disposed on the second photoabsorbing layer, wherein
the first photoabsorbing material is a plurality of two-dimensional (2D) nanosheets and the second photoabsorbing material is a plurality of 2D quantum dots (QDs), or
the first photoabsorbing material is a plurality of 2D QDs and the second photoabsorbing material is a plurality of 2D nanosheets.

2. The heterostructure photodetector of claim 1, further comprising a transition layer disposed between the first photoabsorbing layer and the second photoabsorbing layer, the transition layer comprising a combination of the first photoabsorbing material and the second photoabsorbing material.

3. The heterostructure photodetector of claim 1, wherein each of the first photoabsorbing layer and the second photoabsorbing layer further comprise one or more charge transport materials.

4. The heterostructure photodetector of claim 1, wherein the first photoabsorbing material has a valence band and a conduction band which is offset from a valence band and a conduction band of the second photoabsorbing material to create a built-in electric field.

5. The heterostructure photodetector of claim 1, wherein the first photoabsorbing layer and the second photoabsorbing layer have a combined thickness ranging from about 50 nm to about 800 nm.

6. The heterostructure photodetector of claim 1, wherein the first photoabsorbing layer and the second photoabsorbing layer have a combined thickness ranging from about 100 nm to about 700 nm.

7. The heterostructure photodetector of claim 1, wherein the first photoabsorbing layer and the second photoabsorbing layer have a combined thickness ranging from about 200 nm to about 600 nm.

8. The heterostructure photodetector of claim 1, wherein one of the first photoabsorbing layer and the second photoabsorbing layer further comprise a charge transport material.

9. The heterostructure photodetector of claim 1, wherein the 2D nanosheets have a thickness between 1 to 10 atomic or molecular monolayers and lateral dimensions extending beyond the quantum confinement regime.

10. The heterostructure photodetector of claim 1, wherein the first photoabsorbing layer contains between about 10 vol % to about 95 vol % of the plurality of 2D QDs, and the second photoabsorbing layer contains between about 10 vol % to about 95 vol % of the plurality of 2D nanosheets; or
the first photoabsorbing layer contains between about 10 vol % to about 95 vol % of the plurality of 2D nanosheets, and the second photoabsorbing layer contains between about 10 vol % to about 95 vol % of the plurality of 2D QDs.

11. The heterostructure photodetector of claim 10, wherein each of the first photoabsorbing layer and the second photoabsorbing layer further comprise one or more charge transport materials.

* * * * *